United States Patent
Link et al.

(10) Patent No.: US 10,801,061 B1
(45) Date of Patent: Oct. 13, 2020

(54) SYSTEM AND METHOD FOR FORMING AN EMULSION

(71) Applicant: Bio-Rad Laboratories, Inc., Hercules, CA (US)

(72) Inventors: Darren R. Link, Lexington, MA (US); Patrick Odoy, Rowley, MA (US); Akim Lennhoff, Cambridge, MA (US); John Luckey, Chelmsford, MA (US); Xinyu Li, Bedford, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 274 days.

(21) Appl. No.: 15/909,606

(22) Filed: Mar. 1, 2018

Related U.S. Application Data

(62) Division of application No. 15/259,798, filed on Sep. 8, 2016.

(60) Provisional application No. 62/215,465, filed on Sep. 8, 2015.

(51) Int. Cl.
   *C12Q 1/686* (2018.01)
   *B01J 13/00* (2006.01)

(52) U.S. Cl.
   CPC ............ *C12Q 1/686* (2013.01); *B01J 13/00* (2013.01)

(58) Field of Classification Search
   CPC .. B01F 9/0025; B01F 11/0017; B01F 11/005; B01J 13/00
   See application file for complete search history.

(56) References Cited

U.S. PATENT DOCUMENTS

| | | | |
|---|---|---|---|
| 5,299,864 A * | 4/1994 | Reynolds | B01F 9/0016 366/233 |
| 6,659,637 B2 * | 12/2003 | Friedman | B01F 11/0022 366/110 |
| 8,748,102 B2 | 6/2014 | Berka et al. | |
| 8,790,876 B2 | 7/2014 | Leamon et al. | |
| 9,074,242 B2 | 7/2015 | Larson et al. | |
| 2010/0136544 A1 | 6/2010 | Agresti et al. | |
| 2011/0059435 A1 | 3/2011 | Vogelstein et al. | |
| 2011/0077169 A1 | 3/2011 | McKernan et al. | |
| 2011/0086780 A1 | 4/2011 | Colston, Jr. et al. | |
| 2013/0164400 A1 * | 6/2013 | Knopov | A61K 9/1272 425/5 |
| 2013/0164789 A1 | 6/2013 | Schultz et al. | |

(Continued)

FOREIGN PATENT DOCUMENTS

WO     2010117461 A2    10/2010

OTHER PUBLICATIONS

Shah et al., "Designer emulsions using microfluidics," materialstoday, Apr. 2008, pp. 18-27, vol. 11, No. 4.

(Continued)

*Primary Examiner* — Anshu Bhatia
(74) *Attorney, Agent, or Firm* — Kilyk & Bowersox, P.L.L.C.

(57) ABSTRACT

Systems and methods are provided for forming emulsions from an aqueous fluid and oil. The aqueous fluid-in-oil emulsions are useful for numerous molecular biology techniques. The system is configured to cyclically translate a chamber containing the emulsion components, along a cycle path, while maintaining the axial orientation of the chamber with respect to a horizontal plane, and without rotating the chamber.

19 Claims, 5 Drawing Sheets

(56) References Cited

U.S. PATENT DOCUMENTS

2015/0003183 A1* 1/2015 Meles ................ B01F 11/0005
366/110

OTHER PUBLICATIONS

Peeran et al., "Development and evaluation of water-in-oil formulation of Pseudomonas fluorescens (FP7) against Colletotrichum musae incitant of anthracnose disease in banana" European Journal of Plant Pathology 138: 167-180 (Nov. 24, 2013).

* cited by examiner

SYSTEM AND METHOD FOR FORMING AN EMULSION

CROSS-REFERENCE TO RELATED APPLICATION

This application is a divisional of U.S. patent application Ser. No. 15/259,798, now allowed, filed Sep. 8, 2016, which in-turn claims benefit of U.S. Provisional Application No. 62/215,465 filed Sep. 8, 2015, both of which are incorporated herein by reference in their entireties.

FIELD

The application is related to methods, devices, and systems to generate emulsions, for example, oil-in-water droplets. The provided emulsions can function as microreactors to carry out a variety of biological and/or chemical reactions such as polymerase chain reaction (PCR).

BACKGROUND

An emulsion is a mixture of two immiscible liquids, where one liquid is dispersed in the form of small drops in another liquid that forms a continuous phase. Most conventional methods for making emulsions involve drop breakup using shear or impact stresses generated by manual or mechanical agitation. However, such stresses are not uniform across the system, nor are they finely controlled. Emulsions formed in these ways thus consist of drops that are highly polydisperse in size (Shah et al., Materials Today, 2008, 11, 18-27). Microfluidic devices offer an alternate and versatile route to produce emulsions.

Water and oil emulsions have been found to be useful in numerous molecular biology techniques. For example, enzymatically catalyzed amplification of single nucleic acid molecules in emulsion droplets have found use in DNA sequencing and the generation of libraries of compounds for screening. Such water in oil emulsions been generated by microfluidic systems and by bulk emulsification by agitating the water and oil mixture. Such bulk emulsification has been performed in a filtration apparatus and by use of test tube vortexers, e.g., VWR® multi-tube vortexer. Examples of systems for generating emulsions for use in molecular biology processes can be found in US 2013/0164789 A1, US 2013/0164789 A1, and WO 2010/117461 A2. Such techniques have been inefficient and hard to replicate for the reliable production of droplets suitable for molecular biology techniques such as DNA amplification by PCR. The inventors have created new techniques and instruments for reliably making aqueous in oil emulsions of various droplet sizes with high efficiency and high uniformity of droplet size.

SUMMARY

According to one or more embodiments of the present invention, a method of producing an aqueous fluid-in-oil emulsion is provided. The method may comprise the steps of introducing an aqueous fluid and a continuous phase fluid or oil, that is immiscible with the aqueous fluid, into a chamber, and translating the chamber along a cycle path for a plurality of cycles. The density of the continuous phase fluid may be greater than that of the aqueous fluid. The cycle path may comprise at least a path portion disposed on a plane of movement that is angled with respect to a horizontal plane. The translating may comprise maintaining the chamber in a fixed or variable orientation with respect to the horizontal plane, throughout the entire cycle path. The chamber may have a central axis and the fixed orientation may comprise an orientation where the central axis is, for example, perpendicular to the horizontal plane. The cycle path may be a two-dimensional path entirely on the plane of movement. The translating may comprise moving the chamber in Y axis directions and X axis directions on the plane of movement, or back-and-forth along two axes that are perpendicular to one another, lying on the plane of movement. The cycle path may be a three-dimensional path and the translating may comprise moving the chamber in both Y axis directions and X axis directions on the plane of movement and moving the chamber in Z axis directions toward and away from the plane of movement. The translating may comprise moving the chamber in Z axis directions, toward, away from, and through the plane of movement. The chamber may be maintained oriented substantially vertically or perfectly vertically throughout the entire cycle path. The cycle path may have at least a Y axis movement, that is, include at least a vertical component, whether or not it also includes an X axis component and/or a Z-axis component.

The translating may comprise oscillating the chamber along a first path, wherein oscillating is understood to mean moving around a cycle path, not necessarily on a single axis of movement. The cycle path may include a first path and a second path. The first path may be defined by the formula A $\sin(\omega_1 \cdot t)$, where A is the amplitude of the oscillation, $\omega_1$ is $2\pi$ over the frequency of oscillation, and t is time. The method may involve further translating the chamber in a direction perpendicular to the first path, along a second path defined by the formula B $\sin(\omega_2 \cdot t)$, where B is the amplitude of the translation in a direction perpendicular to A, $\omega_2$ is $2\pi$ over the frequency of oscillation, and t is time. For an exemplary cycle path, $\omega_2$ equals $\omega_1$. The oscillation of the chamber may occur substantially along a vertical axis as defined by a direction that is normal to a horizontal surface. The cycle path is not necessarily perpendicular to the horizontal plane and in some embodiments it is not perpendicular to the horizontal plane. The plane of movement of the cycle path may be tilted relative to the horizontal plane, for example, tilted at least 15 degrees relative to the horizontal plane, tilted at least 30 degrees relative to the horizontal plane, tilted at least 45 degrees relative to the horizontal plane, tilted at least 60 degrees relative to the horizontal plane, or tilted at least 75 degrees relative to the horizontal plane. By avoiding rotation of the chamber, the chamber contents are not subject to constant centrifugal forces that would otherwise tend to separate the aqueous fluid from the denser continuous phase fluid.

The chamber may comprise a plurality of distinct individual chambers. The introducing may comprise introducing the aqueous fluid and the continuous phase fluid into the plurality of chambers, and translating all of the plurality of chambers along the cycle path, for example, simultaneously. The chamber may comprise a plurality of chambers and the introducing may comprise introducing the aqueous fluid into at least one of the chambers and introducing different aqueous fluids into different ones of the chambers. The introducing may comprise introducing one or more different aqueous fluids into the plurality of chambers, introducing the continuous phase fluid into each of the plurality of chambers, and translating all of the plurality of chambers along the cycle path. The plurality of chambers may comprise wells in a microtitre plate. The plurality of chambers may comprise separate containers that are independent of one another. The chamber may comprise a plurality of chambers and each chamber of the plurality of chambers may have a volume of less than 10 milliliters, for example, a volume of less than 1 milliliter or a volume of less than 100 microliters. The ratio of the volume of aqueous fluid to the volume of continuous phase fluid in the chamber may be from 1:1 to 1:20, for example, from 1:1 to 1:2. Conversely, the ratio of the volume of continuous phase fluid to the volume of aqueous phase fluid in the chamber may be from 1:1 to 1:20, for example, from 1:1 to 1:2.

The translating may comprise moving the chamber along the cycle path at a speed of at least 500 cycles per minute, for example, at a speed of at least 1000 cycles per minute, or at a speed of at least 5000 cycles per minute. The cycle path may comprise a circular path or it may have a different shape. The translating may be carried out for at least one minute, for example, for at least 3 minutes or for at least 5 minutes.

The aqueous fluid may comprise or contain a DNA polymerase. The aqueous fluid may further comprise at least one pair of amplification primers. After formation of an emulsion in the chamber, the emulsion and/or droplets from the emulsion may be subject to one or more biological reactions, such as polymerase chain reaction.

The present invention also provides a system for producing an aqueous fluid-in-oil emulsion. The system may comprise a mounting frame, a drive train, and a chamber platform. The drive train may include a drive motor mounted on the mounting frame. The chamber platform may be connected to the drive train and the drive train may be configured to move the chamber platform along a cycle path. The cycle path may include a vertical component and the chamber platform may be connected to the drive train through a swiveling connection. The drive motor may comprise a variable speed drive motor. The drive train may comprise a rotatable circular disk and an off-centered swivel mount mounted to the rotatable circular disk for swiveling motion. The chamber platform may comprise at least two mounting pins secured to the off-centered swivel mount. The cycle path may be on a plane of movement that is tilted with respect to a horizontal surface, for example, the plane of movement may be tilted at an angle of from about 15 degrees to about 75 degrees with respect to the horizontal surface, or tilted at an angle of from about 30 degrees to about 60 degrees with respect to the horizontal surface.

BRIEF DESCRIPTION OF DRAWINGS

The above and further features will be more clearly appreciated from the following detailed description when taken in conjunction with the accompanying drawings. All of these conventions, however, are intended to illustrate, rather than limit, the present teachings.

FIG. 3 also shows the chamber after it has been moved or translated through multiple cycles of translation, to form an emulsion in the chamber.

DETAILED DESCRIPTION

Figure 1A:
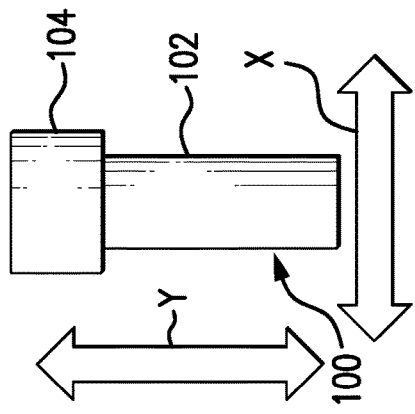
FIG. 1A shows a chamber 100 and an oscillating movement along a single axis (the Y axis).

Provided herein are methods and systems for generating aqueous fluid-in-oil emulsions. Such aqueous fluid-in-oil emulsions as provided herein are useful for numerous molecular biology techniques, as well as other uses. Various embodiments of the subject invention utilize an aqueous fluid and a continuous phase fluid that is immiscible with the aqueous fluid. In one or more embodiments, the continuous phase fluid has a higher density than the density of the aqueous fluid. The subject methods involve moving a chamber or chambers, each containing an aliquot of the continuous phase fluid and an aliquot of the aqueous fluid, through a cycle of translation without rotating the chamber or chambers. In one or more embodiments, the chamber containing the aqueous fluid and the continuous phase fluid is cycled along a continuous path of movement substantially within a plane, herein referred to as a plane of movement. The plane of movement is neither horizontal nor parallel to a level surface upon which a device is located for moving, or cyclically translating, the chamber.

In some embodiments, the plane of movement may be perpendicular to the surface upon which the device is located. In some embodiments the plane of movement is tilted at least 30 degrees relative to a level or horizontal surface. In some embodiments the plane of movement is tilted at least 35 degrees relative to a level or horizontal surface. In some embodiments the plane of movement is tilted at least 40 degrees relative to a level or horizontal surface. In some embodiments the plane of movement is tilted at least 45 degrees relative to a level or horizontal surface. In some embodiments the plane of movement is tilted at least 50 degrees relative to a level or horizontal surface. In some embodiments the plane of movement is tilted at least 55 degrees relative to a level or horizontal surface. In some embodiments the plane of movement is tilted at least 60 degrees relative to a level or horizontal surface. In some embodiments the plane of movement is tilted at least 65 degrees relative to a level or horizontal surface. In some embodiments the plane of movement is tilted at least 70 degrees relative to a level or horizontal surface. In some embodiments the plane of movement is tilted at least 75 degrees relative to a level or horizontal surface. In some embodiments the plane of movement is tilted at least 80 degrees relative to a level or horizontal surface. In some embodiments the plane of movement is tilted at least 85 degrees relative to a level or horizontal surface. In some embodiments the plane of movement is tilted at least 90 degrees relative to a level or horizontal surface.

Although a group, set, rack, collection, or other plurality of chambers can simultaneously be cycled along a path, the invention can be exemplified with reference to the cyclical translation of a single chamber. The continuous path of movement upon which the chamber is translated in a given cycle may take on a variety of shapes. The path for the cycle, herein referred to as the cycle path, may be or include a variety of closed curves. The curve may be a simple closed curve, i.e., a curve that does not cross itself. Exemplary closed curves can comprise a circle, an ellipse, an oval, a polygon, a racetrack, or the like. In some embodiments the cycle path along which the chamber is translated can be defined by $A \sin(\omega_1 \cdot t)$, where A is the amplitude of the oscillation, $\omega_1$ is $2\pi$ over the frequency of oscillation, and t is time. In some embodiments the cycle path for translating the chamber in a direction perpendicular to the first direction along a path defined by $B \sin(\omega_2 \cdot t + \varphi)$, where B is the amplitude in the perpendicular direction (along the X axis), $\omega_2$ is $2\pi$ over the frequency of the cycle, and t is time, and $\varphi$ is phase. The two oscillations can be out of phase so as to produce movement along a curved path. In such embodiments, $\varphi$ is not equal to 0, e.g., it is in the range of greater than 0 to less than or equal to 90 degrees.

In one or more embodiments the chamber is not rotated during its movement along the cycle path. In some embodiments, the chamber is in a fixed position on a platform that serves to move the chamber. The chamber can maintain the same vertical orientation, tilt, or axial positioning throughout the entire cycle path. In some embodiments there is no axis of rotation running through the chamber or chambers.

The chamber may have any of a variety of configurations. In some embodiments the chamber may have a major axis along its longest dimension. In such embodiments the chamber may be maintained in a vertical position, with respect to its major axis, during the movement along the cycle path.

In some embodiments, a plurality of chambers may be co-transported along the cycle path at the same time. Each of the plurality of chambers may form part of a single unit, such as a microtitre plate. In other embodiments, each of the plurality of chambers may be independent of the other chambers, for example, the plurality of chambers can comprise a plurality of Eppendorf tubes held by a plate or platform. Each of the plurality of chambers can be maintained in a relative position with respect to the other chambers of the plurality, for example, such that it stays a fixed distance away from adjacent chambers throughout the entire cycle path. The chambers may be sealed so as to prevent loss of contents during cycling. Each chamber can be independently sealed. Two or more, or all, of a plurality of chambers can be sealed by a common sealing plate, film, heat-seal layer, or other structure.

In the subject methods, the chamber is translated along a single cycle path at a speed that is sufficient to produce an emulsion having desired characteristics. Similarly, the time spent for cycling, i.e., completing a single cycle path, is selected so as to be sufficient to produce an emulsion having desired characteristics. Typically, the speed of cycling is at least 500 cycles per minute. In some embodiments the speed is at least 1000 cycles per minute. In some embodiments the speed is at least 2000 cycles per minute. In some embodiments the speed is at least 3000 cycles per minute. In some embodiments the speed is at least 4000 cycles per minute. In some embodiments the speed is at least 5000 cycles per minute. The cycling speed may be within a desired range of speeds, for example, within the range of from 400 to 10,000 cycles per minute, from 500 to 5000 cycles per minute, from 1000 to 4000 cycles per minute, or from 2000 to 3000 cycles per minute.

In some embodiments the cycling takes place for at least one minute. In some embodiments the cycling takes place for at least two minutes. In some embodiments the cycling takes place for at least three minutes. In some embodiments the cycling takes place for at least four minutes. In some embodiments the cycling takes place for least five minutes. The cycling may take place within a range of times, for example, for a time within the range of from 30 seconds to 10 minutes, from 1 minute to 8 minutes, from 2 minutes to 5 minutes, or from 3 minutes to 4 minutes.

The ratio of the aqueous fluid to the continuous phase fluid, in the chamber, may vary significantly. Examples of such ratios, expressed in volume-to-volume terms, may be, for example, 1:1, 1:2, 1:3, 1:4, 1:6, 1:7, 1:8, 1:9, 1:10, 1:11, 1:12, 1:13, 1:14, 1:15, 1:16, 1:17, 1:18, 1:19, and 1:20. The invention also includes embodiments in which the ratio of the continuous phase fluid to the aqueous fluid, may be, for example, 1:1, 1:2, 1:3, 1:4, 1:6, 1:7, 1:8, 1:9, 1:10, 1:11; 1:12, 1:13, 1:14, 1:15, 1:16, 1:17, 1:18, 1:19, and 1:20, again in terms of volume-to-volume ratios.

The volume of the droplets formed in the emulsion may be within a wide variety of ranges, including, but not limited to, from 1 picoliter to 100 nanoliters per droplet. Typically, emulsions useful for molecular biology techniques may comprise droplets each having a volume of less than 1 nanoliter, for example, in the range of from 1 picoliter to 100 picoliters. In some embodiments, at least 50% of droplets formed in a given emulsion prepared in accordance with the present invention are of the desired volume. In some embodiments at least 80% of the droplets are of the desired volume. In some embodiments at least 90% of the droplets are of the desired volume. In some embodiments at least 95% of the droplets are of the desired volume. In some embodiments at least 99% of the droplets are of the desired volume. Preferably, the variation in volume between the droplets in an emulsion preparation obtained by the subject methods is less than 10% variation in size (i.e., volume) between droplets. In some embodiments the variation in size is less than 5% between droplets. In some embodiments the variation in size is less than 1% between the droplets.

The emulsions provided by the subject invention have a variety of uses, particularly in molecular biology techniques, including, but not limited to, PCR, digital PCR, DNA sequencing, and the like. Examples of such techniques can be found in US 2011/0077169 A1 (Reagents, Methods, And Libraries For Bead-based Sequencing), U.S. Pat. No. 8,748, 102 B2 (Bead Emulsion Nucleic Acid Amplification), U.S. Pat. No. 8,790,876 B2 (Methods Of Amplifying And Sequencing Nucleic Acids), US 2010/0136544 A1 (Assays And Other Reactions Involving Droplets), and US 2011/ 0059435 A1 (Methods For Beaming). Applicants have discovered that surprisingly superior results in the quality of DNA sequencing uniformity can be obtained by using emulsions produced by the subject methods as applied to the sequencing of PCR amplification products produced using the multi-primer pair PCR amplification methods described in U.S. Pat. No. 9,074,242 B1. In some embodiments, primers can be multiplexed in solution to be at uniform concentration all droplets formed in the emulsion and the target DNA for amplification or sequencing can be present at concentration such that only one target is amplified in a droplet.

The aqueous fluid in the chamber may be a solution or other liquid and may contain a variety of reagents useful for molecular biology techniques. Such reagents include enzymes (for example, enzymes having DNA polymerase activity), nucleotide triphosphates, buffers, nucleic acid samples for amplification, and amplification primers. Molecular biology techniques such as DNA amplification, digital PCR, real-time PCR, DNA sequencing, mini sequencing, and the like, are well known to persons of ordinary skill in the art and may be carried out in emulsions formed by the methods and systems of the present invention. One or more reactants, reagents, or components for enabling one or more of such techniques may be readily incorporated into the aqueous fluid added to the chamber.

In the embodiments described herein, droplets of an emulsion may be referred to as compartments, microcapsules, microreactors, microenvironments, or other names commonly used in the related art. The droplets may be aqueous droplets and may range in size depending on the composition of the emulsion components, the contents contained therein, and the formation technique employed. The described emulsions are microenvironments within which chemical reactions may be performed. The chemical reactions may include binding reactions, such as Reverse Transcription, PCR, or other processes. For example, template nucleic acids and all reagents necessary to perform a desired PCR reaction may be encapsulated and chemically isolated in a droplet of an emulsion. In one or more embodiments not every droplet in the emulsion necessarily contains all of the components necessary to carry out a desired reaction. In some embodiments, the amount of one or more components necessary to carry out a particular reaction is chosen to cause a likelihood that not all of the droplets in the resulting emulsion contain all the necessary components for the reaction. Digital PCR is exemplary of such techniques. Additional surfactants or other stabilizing agents may be employed in some embodiments to promote additional stability of the droplets as described above. Thermocycling operations typical of PCR methods may be executed using the droplets to amplify an encapsulated nucleic acid template, resulting in the generation of a population comprising many substantially identical copies of the template nucleic acid. In some embodiments, the population within the droplet may be referred to as a "clonally isolated," "compartmentalized," "sequestered," "encapsulated," or "localized" population. Also in the present example, some or all of the described droplets may further encapsulate a solid substrate such as a bead. In some embodiments, beads may be employed for attachment of a template, amplified copies of the template, amplified copies complementary to the template, or a combination thereof. Further, the solid substrate may be enabled for attachment of one or more other types of nucleic acids, reagents, labels, or other molecules of interest. Herein, "aqueous fluid" is not meant to be limited to solutions but instead also encompasses aqueous fluids that contain such solid substrates, beads, and the like. The term "aqueous fluid" may encompass suspensions and mixtures containing such solids. In some embodiments, the emulsion droplets may comprise relatively long molecules of DNA (or RNA), such molecules can be longer than 10 kb, 20 kb, 50 kb, 100 kb, 200 kb, 500 kb, or longer, as well as the various intermediate sizes.

It will also be appreciated that the embodiments described herein are not limited to encapsulating nucleic acids in droplets, but rather the droplets may be configured to encapsulate a variety of entities that include, but are limited to, cells, sperm cells, eggs, single-cell organisms, antibodies, enzymes, proteins, combinations thereof, and the like. As with nucleic acids, the droplets may further be amenable to performing various reactions on the entities encapsulated therein and/or for detection methods.

The terms "digital polymerase chain reaction," "digital PCR," or "dPCR," as used herein, generally refer to a precise method to clonally amplify and quantify nucleic acids including DNA, cDNA, or RNA, by partitioning target nucleic acids into a large number of separate compartments inside one or more of which a target nucleic acid is amplified and can be detected.

Some exemplary embodiments of systems and methods associated with sample preparation and processing, generation of data, and analysis of data are generally described below, some or all of which are amenable for use with embodiments of the presently described invention. In particular, the exemplary embodiments of the systems and methods of the present invention can be used for the preparation of nucleic acid template molecules, amplification of template molecules, and detection of template molecules and/or substantially identical copies thereof. Embodiments that execute methods of detection such as digital PCR and/or sequencing methods utilizing exemplary instrumentation and computer systems, are also described herein and are within the scope of the present invention.

An exemplary embodiment of an "emulsion" is a stable emulsion of two immiscible substances. The embodiments described herein generally refer to an emulsion of aqueous droplets dispersed in a continuous oil phase and within which reactions may occur. In particular, the aqueous droplets of an emulsion amenable for use in methods for conducting reactions with biological samples, and detecting products, may include a first fluid, such as a water-based fluid (typically referred to as an "aqueous" fluid) suspended or dispersed as droplets (also referred to as a discontinuous phase) within another fluid, such as a hydrophobic fluid (also referred to as a continuous phase fluid) that typically includes some type of oil and that forms a continuous phase of the emulsion. Examples of oils that may be employed include, but are not limited to, mineral oils, silicone-based oils, fluorinated oils, partially fluorinated oils, or perfluorinated oils.

One example of an aqueous fluid that may be used in accordance with embodiments of the invention may include an aqueous buffer solution, such as ultrapure water (e.g., 18 mega-ohm resistivity, obtained, for instance by column chromatography), 10 mM Tris HCl, and one or more of 1 mM EDTA (TE) buffer, phosphate buffer saline (PBS), or acetate buffer. In the presently described example, any liquid or buffer that is physiologically compatible with nucleic acid molecules or an encapsulated biological entity can be used. Also, in the same or in alternative examples, a continuous phase fluid that can be used in accordance with embodiments of the invention includes a non-polar solvent, decane (e.g., tetradecane or hexadecane), a fluorocarbon oil, a silicone oil, or another oil, for example, mineral oil. The oil is preferably, however, of a greater density than the aqueous fluid. In certain embodiments, the carrier fluid may contain one or more additives, such as agents which increase, reduce, or otherwise create or change non-Newtonian surface tensions (surfactants) and/or stabilize droplets against spontaneous coalescence on contact.

Embodiments of surfactants that act to stabilize emulsions, which may be particularly useful for embodiments that include conducting reactions with biological samples, such as PCR, may include one or more of a silicone or fluorinated surfactant. For example, in microfluidic embodiments the addition of one or more surfactants can aid in controlling or optimizing droplet size, flow, and uniformity, for example, by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils and substantially reduce the likelihood of droplet coalescence. Exemplary surfactants include amphiphilic molecules such as lipids and detergents, polymers, block-copolymers, proteins, nano-particles and other additives that are known to stabilize droplets against spontaneous coalescence.

In some embodiments, the aqueous droplets may be coated with a surfactant or a mixture of surfactants, where those of skill in the art understand that surfactant molecules typically reside at the interface between immiscible fluids, and in some cases form micelles in the continuous phase when the concentration of surfactant(s) is greater than what is referred to as the critical micelle concentration (also sometimes referred to as CMC). Examples of surfactants that may be added to the carrier fluid include, but are not limited to, surfactants such as sorbitan-based carboxylic acid esters (e.g., the "Span" surfactants, available from Fluka Chemika, Buchs, Switzerland), including sorbitan monolaurate (Span 20), sorbitan monopalmitate (Span 40), sorbitan monostearate (Span 60), and sorbitan monooleate (Span 80), and perfluorinated polyethers (e.g., DuPont Krytox 157 FSL, FSM, and/or FSH, available from E.I. du Pont de Nemours and Company, Wilmington, Del.). Other non-limiting examples of non-ionic surfactants that may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, and the like) and alkanolamines (e.g., diethanolamine-fatty acid condensates and isopropanolamine-fatty acid condensates).

In one or more embodiments, a fluorosurfactant can be prepared by reacting the perflourinated polyether DuPont Krytox 157 FSL, FSM, or FSH with aqueous ammonium hydroxide in a volatile fluorinated solvent. The solvent, residual water, and ammonia can be removed with a rotary evaporator. The surfactant can then be dissolved (e.g., to obtain a concentration of 2.5 wt %) in a fluorinated oil (e.g., Flourinert (3M)), which then serves as the continuous phase fluid or carrier fluid (e.g., the continuous phase of the resulting emulsion). In the presently described embodiment, the surfactant produced is an ionic salt, and it will be appreciated that other embodiments of non-ionic surfactant compositions may also be used. For example, non-ionic surfactant compositions that may be used may include what are referred to as block copolymers (e.g. di-block, or tri-block copolymers) typically comprising a head group and one or more tail groups. In some embodiments, the surfactant may be non-ionic, e.g, non-ionic perflourinatade polyether-polyethylene glycol, [PFPE-PEG], diblock or tri-block copolymers. A more specific example of a fluorinated block copolymer includes a polyethylene glycol (PEG) head group and one or more perfluoropolyether (PFPE) tail groups.

Further, in some embodiments other reagents that act as droplet stabilizers (also referred to as passivating agents) may be included. Useful droplet stabilizing reagents may include, but are not limited to, polymers, proteins, BSA, spermine, and PEG. The emulsions produced may be stable and the droplets may be sufficiently stable so as to be introduced onto a microfluidic system.

In some embodiments, desirable characteristics may be achieved by adding a second surfactant, or other agent, such as a polymer or other additive, to the aqueous fluid. Further, in certain embodiments utilizing microfluidic technology, the continuous phase fluid may be caused to flow through an outlet channel so that the surfactant in the continuous phase fluid coats the outlet channel walls.

The emulsion droplets can contain cells or beads. Various concentrations, volume-to-volume percentages, and/or weight-to-weight percentages between an estimated number of droplets and the number of cells or beads used can be calculated and implemented so that a certain percentage of the droplets will contain at least on cell or bead, more than one cell or bead, one cell or bead, or the like. The emulsion can be prepared from components or aqueous fluids such that the droplets contain one or more reagents, for example, one or more antibodies, one or more oligonucleotides, a combination thereof, or the like. The reagents can be attached to the surfaces of beads. The reagents can be releasably attached to the surfaces of the beads, or securely attached. The beads can be dissolvable, for example, such that the beads dissolve and release reagents. One or beads may be in emulsion droplets. Beads can be used to deliver primers, e.g, by using beads that comprise primers hybridized to a universal oligonucleotide attached to the bead, wherein a sequence complementary to the universal oligonucleotide is present in the primer. In some embodiments the primers can be released from the bead by cleaving a chemical bonds. In addition to being used to deliver primers, the beads can be used to deliver barcoding sequences, such barcoding sequences can, in some embodiments further comprise one or more primer sequences.

The invention also includes kits for practicing the subject methods. Such kits may include multi-well-plates containing oil, surfactant, master mix and optionally oligonucleotide primers and beads such that an end user is only required to add the sample to the reaction prior to generating the emulsification, and thermal cycling. The kits may also, optionally include other reagants that do not need to be included in an emulsion generation process, e.g, emulsion breaking agents With reference to the drawings, FIG. 1A shows a chamber 100 in the form of a vial 102 that is sealed at the top thereof by a cap 104. After an aqueous fluid and an oil having a density that is greater than the density of the aqueous fluid are introduced into vial 102, cap 104 is secured to vial 102 and chamber 100 is oscillated up and down in Y axis directions as represented by the double-headed arrow. Whether chamber 100 is moving upwardly or downwardly, along the Y axis, the orientation of chamber 100 remains the same, specifically, cap 104 remains vertically above vial 102 at all positions along the oscillating cycle.

Figure 1B:
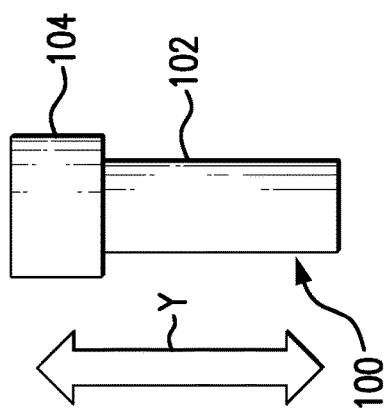
FIG. 1B shows a chamber 100 and movement along both a first axis of motion (along a Y axis) and a second axis of motion (along an X axis) while the chamber maintains a vertical orientation.
Figure 1C:
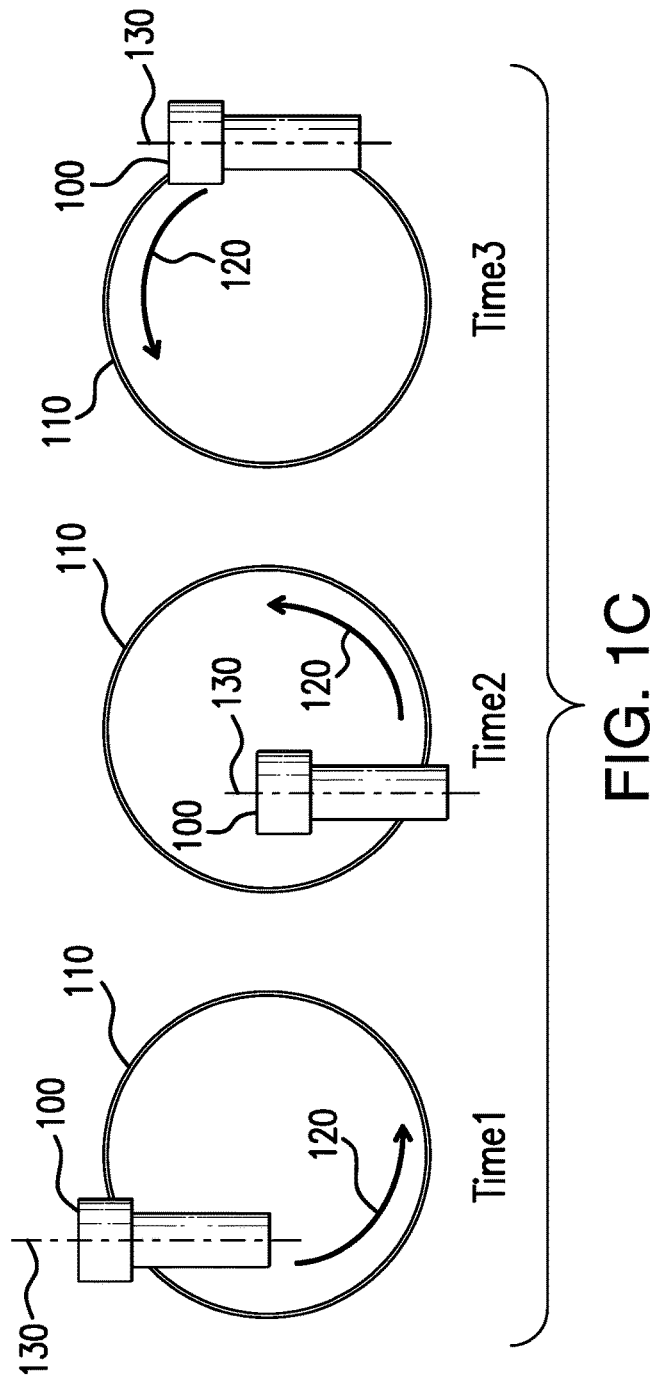
FIG. 1C shows a series of three time points in which a chamber containing an aqueous fluid and a continuous phase fluid, of higher density than the aqueous fluid, is moved such that the chamber is translated along both the X and Y axes through a cycle and within a vertical plane of motion. As can be seen, the chamber remains upright, that is, vertically oriented, throughout the cycle of translation and is not rotated about any axis drawn through the chamber.

FIG. 1B shows the same chamber 100 as shown in FIG. 1A, but depicts movement of the chamber up and down along Y axis directions, and movement back and forth along X axis directions, as depicted by the two double-headed arrows. By changing the amplitudes of the two oscillating motions the cycle path of chamber 100 can take the form of a circular cycle path, an elliptical cycle path, an oval cycle path, or the like. Moreover, the cycle path does not need to be identical for each cycle and thus the amplitude of the oscillation can be varied, from cycle to cycle, along the Y axis, the X axis, or both. While FIG. 1B shows the X axis and the Y axis directions being orthogonal to one another, the directions of oscillation may be, but do not necessarily have to be, orthogonal to one another. FIG. 1C shows chamber 100 oscillating or moving along a circular cycle path 110. Chamber 100 is moved or translated along cycle path 110 in the counterclockwise direction shown by directional arrow 120. FIG. 1C shows chamber 100 in three different positions along cycle path 110 at three different points in time, respectively. Chamber 100 is cylindrical in shape, circular in cross-section, and has a central axis 130. As can be seen in FIG. 1C, the orientation of chamber 100 remains the same along the entire cycle path, at each point in time, with central axis 130 being vertically orientated in each position.

Figure 2:
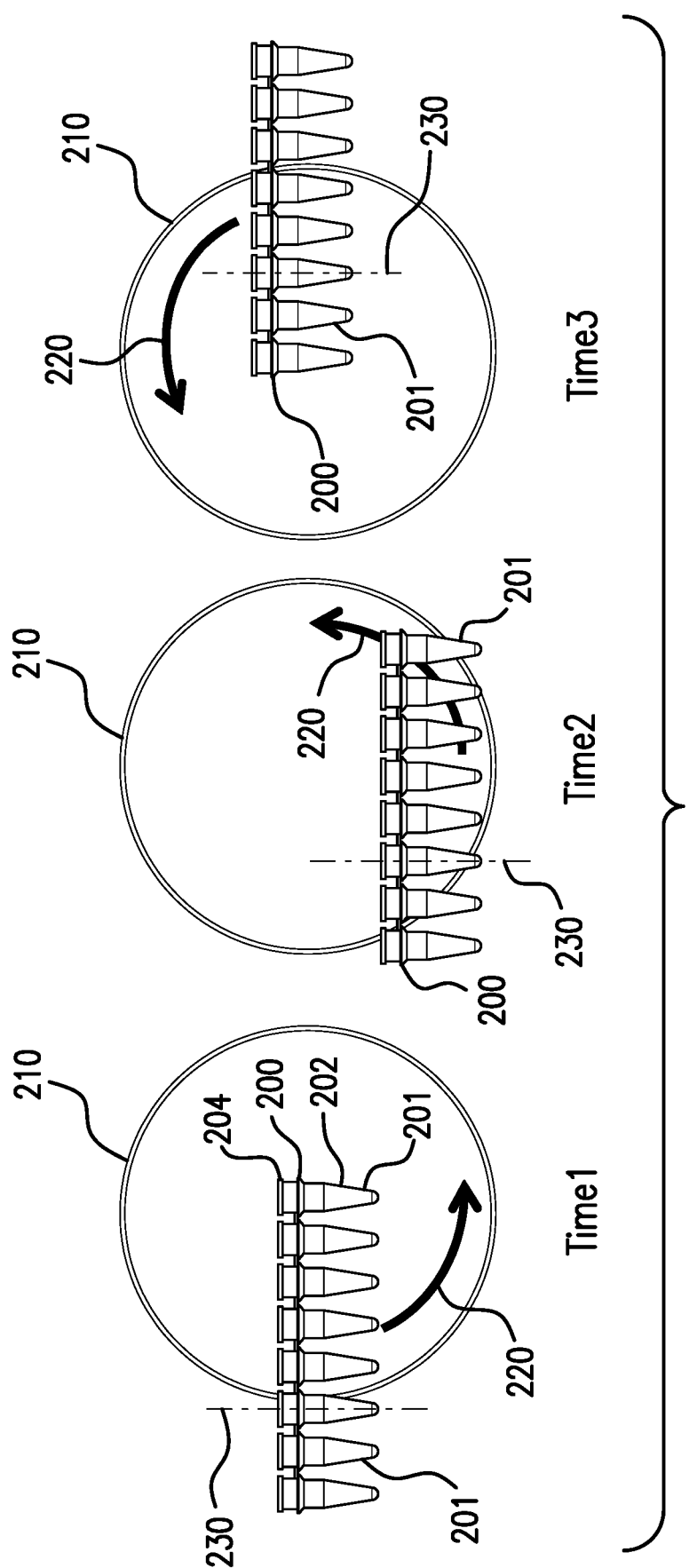
FIG. 2 shows eight chambers in the form of Eppendorf tubes each filled with an aqueous fluid on top and a continuous phase fluid, of greater density than the aqueous fluid, in the bottom. As can be seen, the chambers are moved together and translated along both the X and Y axes through a cycle of translation on a vertical plane of motion. The chambers remain upright, that is, vertically oriented, throughout the cycle of translation and are not rotated about any axis drawn through the chambers.

FIG. 2 is a side view of a multiwell plate 200 being moved or translated along a circular cycle path 210 in accordance with the present invention. Multiwell plate 200 comprises eight wells 201 each in the form of a vial 202 sealed by a cap 204 and integrally formed with or connected to a plate structure that holds, bonds, or otherwise secures the eight wells together. Each well 201 of multiwell plate 200 is vertically oriented, has a circular cross-section, and includes a central axis 230. The central axes 230 of all the wells 201 are parallel to one another, and, as shown, vertically oriented. As can be seen in FIG. 2, as multiwell plate 200 travels along cycle path 210 the orientation of multiwell plate 200, including the vertical orientation of each central axis 230, remains the same along the entire cycle path. FIG. 2 shows the positions of multiwell plate 200 at three points of time along cycle path 210.

Figure 3:
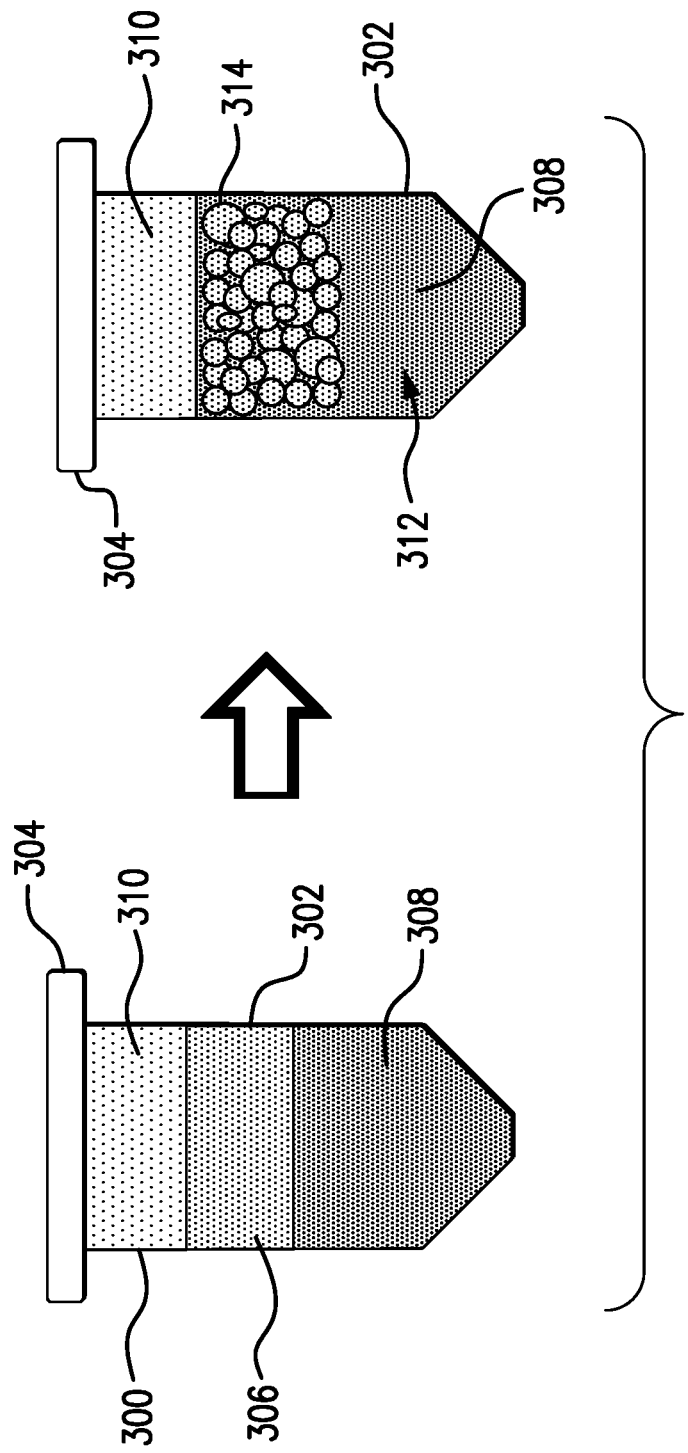
FIG. 3 shows an emulsion-forming process wherein a chamber initially contains an aqueous fluid on top of a continuous phase fluid. The continuous phase fluid is immiscible with respect to the aqueous fluid and has a greater density than the aqueous fluid.

FIG. 3 is schematic representation of a chamber 300 and its contents before and after an emulsion-forming method is carried out in accordance with the present invention. The before view, shown to the left of the arrow, depicts chamber 300 in the form of a vial 302 that is sealed at the top thereof by a cap 304. Inside chamber 300 is provided an aqueous fluid 306 and an oil 308. Oil 308 has a density that is greater than the density of the aqueous fluid 306, and thus, oil 308 sinks and is positioned below aqueous fluid 306. Above aqueous fluid 306 is an air space 310 or head space that may be occupied by gas from the surrounding atmosphere, by an inert gas, by air, by clean dry air, by purified air, or the like.

After chamber 300 is subjected to a plurality of cycles of translation or oscillation in accordance with the present invention, as depicted by the arrow, an emulsion 312 results in chamber 300. As can be seen to the right of the arrow in FIG. 3, emulsion 312 comprises a plurality of droplets 314 of aqueous fluid 306 floating in and above oil 308. Due to the lower density of aqueous fluid 306 compared to the density of oil 308, aqueous fluid droplets 314 form a discontinuous phase of emulsion 312 and float near the top of the continuous phase of emulsion 312, which is formed by oil 308.

Other embodiments of the present invention include devices suitable for performing the subject methods. Such devices can comprise a motor configured to drive the translation of a chamber within a chamber holder and/or a rotatable chamber configured to have an axis of rotation around an axis of rotation that is not perpendicular to a level surface when the device is positioned on a level surface. In some embodiments the rotatable chamber holder is configured to hold a multi-well plate, for example, a microtiter plate, a 96-well plate, a 384-well plate, a 1536-well plate, or the like. In some embodiments the chamber holder holds a microtitre plate. In some embodiments the device may further comprise a speed controller configured to control the speed of the motor. In some embodiments the speed controller may be a variable speed controller capable of adjusting the speed of the motion of the chamber as it progresses through a cycle of motion or translation to complete a cycle path. The chamber holder may be configured so as to maintain the chamber in a substantially vertical position during the course of a cycle translating the chamber along a cycle path.

Various devices and systems can be used to carry out the methods of the present invention and provide the cycle paths, speeds, cycling, and durations described and claimed herein. In an exemplary system, a vortex mixer or microplate vortexer can be mounted on a tilted platform or vertical platform to generate a tilted or vertical plane of movement and thus a tilted or vertical cycle path. A variable speed motor may be used to provide controllable speeds of cycling and amplitude of oscillation. Gears, belts, pulleys, guides, tracks, rails, and the like may be used to provide cycle paths of various shapes and sizes and the cycle path does not need to be limited to a circular shape. Off-centered spinning disks may be implemented to provide a cycle path. An exemplary system for providing an off-centered circular cycle path is shown in FIGS. 1C and 2. Platforms comprising a disc or wheel mounted eccentrically on a revolving shaft may be used to transform rotation into backward-and-forward motion, as with a cam in an internal combustion engine.

The present invention also provides a system for producing an aqueous fluid-in-oil emulsion. The system may comprise a mounting frame, a drive train, and a chamber platform. The drive train may include a drive motor mounted on the mounting frame. The chamber platform may be connected to the drive train and the drive train may be configured to move the chamber platform along a cycle path. The cycle path may include a vertical component and the chamber platform may be connected to the drive train through a swiveling connection. The drive motor may comprise a variable speed drive motor. The drive train may comprise a rotatable circular disk and an off-centered swivel mount mounted to the rotatable circular disk for swiveling motion. The chamber platform may comprise at least two mounting pins secured to the off-centered swivel mount. The swivel mount may provide a swiveling action that enable a chamber held by the chamber platform to maintain a fixed orientation with respect to the horizon, throughout an entire pass along the cycle path, much like the way a Ferris wheel maintains each car of the Ferris wheel in a vertical orientation so that passengers in the cars do not travel upside down as their cars reach the top of the Ferris wheel. Similar to Ferris wheel, the chamber platform does not rotate around the cycle path but rather moves along the cycle path while maintaining a fixed vertical orientation.

The cycle path formed by the drive train may be on a plane of movement that is tilted with respect to a horizontal surface, for example, the plane of movement may be tilted at an angle of from about 15 degrees to about 75 degrees with respect to the horizontal surface, or tilted at an angle of from about 30 degrees to about 60 degrees with respect to the horizontal surface. The swiveling connection enables the chamber platform to maintain a predetermined orientation with respect to a horizontal surface, throughout movement along the entire cycle path. The cycle path may be a circular cycle path along a plane of movement and the plane of movement may be perpendicular to or tilted with respect to a horizontal surface, for example, with respect to a horizontal surface on which the frame and system is located.

A chamber may be secured to the chamber platform. The chamber may comprise a multiwell plate and the multiwell plate may be secured to the chamber platform. The multiwell plate may comprise a plurality of wells and at least one well of the wells of the plurality may contain an aqueous fluid and an oil. The aqueous fluid has a density and the oil has a density that may be greater than the density of the aqueous fluid. The at least one well may be sealed. The chamber may comprise a vial and the vial may be secured to the chamber platform. The vial may contain an aqueous fluid and an oil wherein the aqueous fluid has a density and the oil may have a density that is greater than the density of the aqueous fluid. The vial may be sealed.

The system may include a chamber secured to the chamber platform, wherein the chamber contains an aqueous fluid and an oil, the aqueous fluid has a density, the oil has a density that may be greater than the density of the aqueous fluid, the chamber may be sealed, and the aqueous fluid may contain a DNA polymerase. The aqueous fluid may also contain at least one pair of amplification primers.

Figure 4:
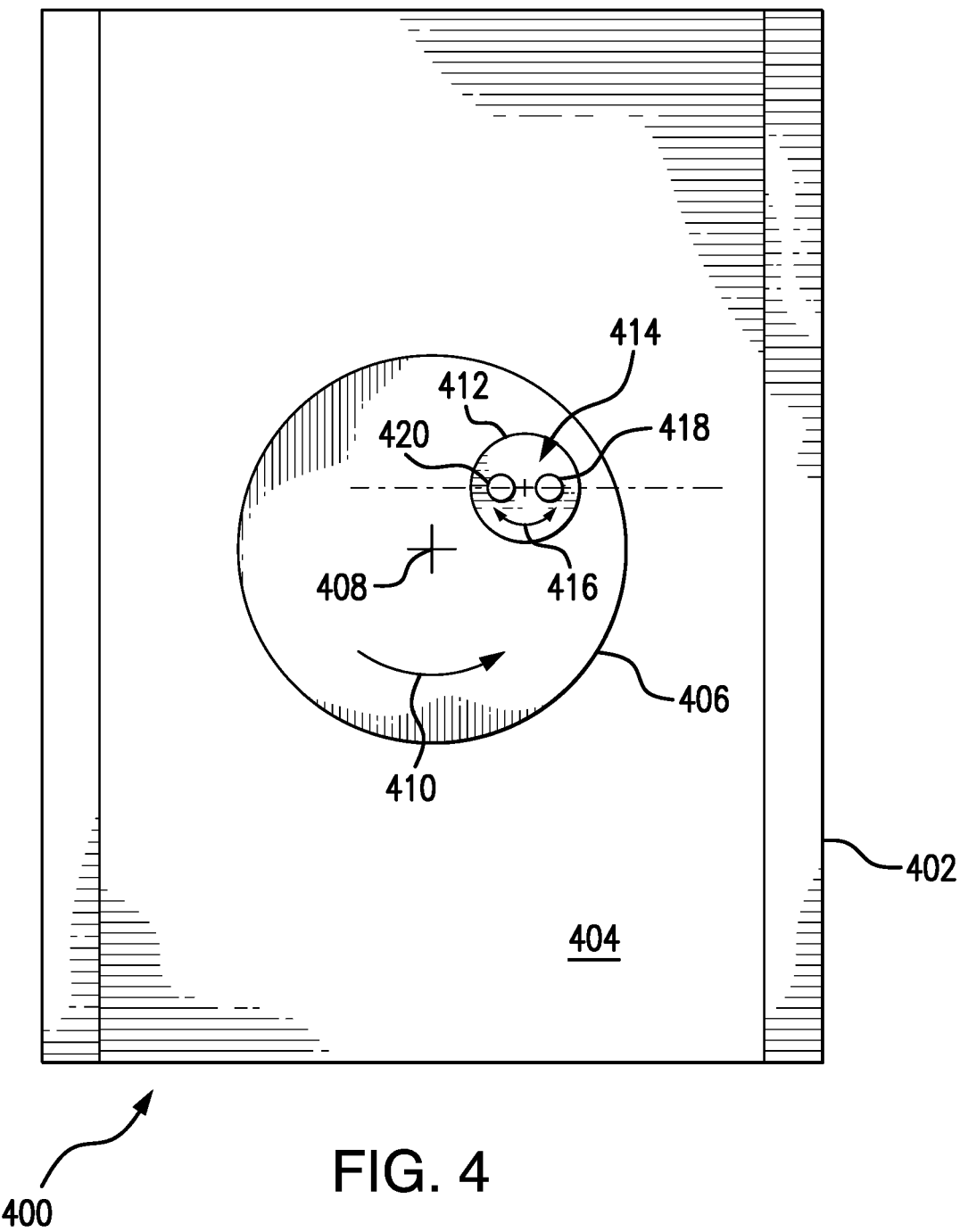
FIG. 4 is a front view of a system in accordance with the present invention, for translating one or more chambers, for example, a multiwell plate, along a circular cycle path on a vertical plane of movement.

FIG. 4 is a front view of a system 400 in accordance with the present invention, for translating one or more chambers, for example, a multiwell plate, along a circular cycle path on a vertical plane of movement. System 400 comprises a frame 402 supporting a vertical mounting plate 404 to which is rotatably mounted a circular disc 406 for rotation for about a central axis of rotation 408. Circular disc 406 is mounting on an axle that also rotates about axis of rotation 408 and is driven by a variable speed drive unit. Circular disc 406 is configured for rotation in a counterclockwise direction as indicated by directional arrow 410 but may also, or instead, be rotated in a clockwise direction. Mounted off-center on circular disc 406 is a mounting disc 412 that is mounted to circular disc 406, for swiveling about a central axis of swivel 414. As indicated by double-headed directional arrow 416, mounting disc 412 can swivel in both clockwise and counterclockwise directions relative to circular disc 406. Mounting disc 412 comprises two mounting pins, 418, 420, that are horizontally aligned with one another and that maintain their horizontal alignment while circular disc 406 rotates about axis of rotation 408. The horizontal alignment of mounting pins 418 and 420 is enabled by the swiveling action of mounting disc 412. Mounting disc 412 can be appropriately weighted to effect a swiveling action during rotation of circular disc 406 and to maintain the horizontal alignment of mounting pins 418 and 420. Mounting pins 418 and 420 can mate with a pair of holes or recesses in a chamber, such as a multiwell plate, to hold the chamber in a vertical orientation during an entire rotation of circular disc 406. For a multiwell plate, mounting pins 418 and 420 can mate with two horizontally aligned recesses or through-holes extending into and/or through a side edge of the mulitwell plate. The multiwell plate can be secured to mounting pins 418 and 420 through a friction fit, a snap fit, a threaded relationship, using threads on the pins and securing nuts, or the like.

Figure 5:
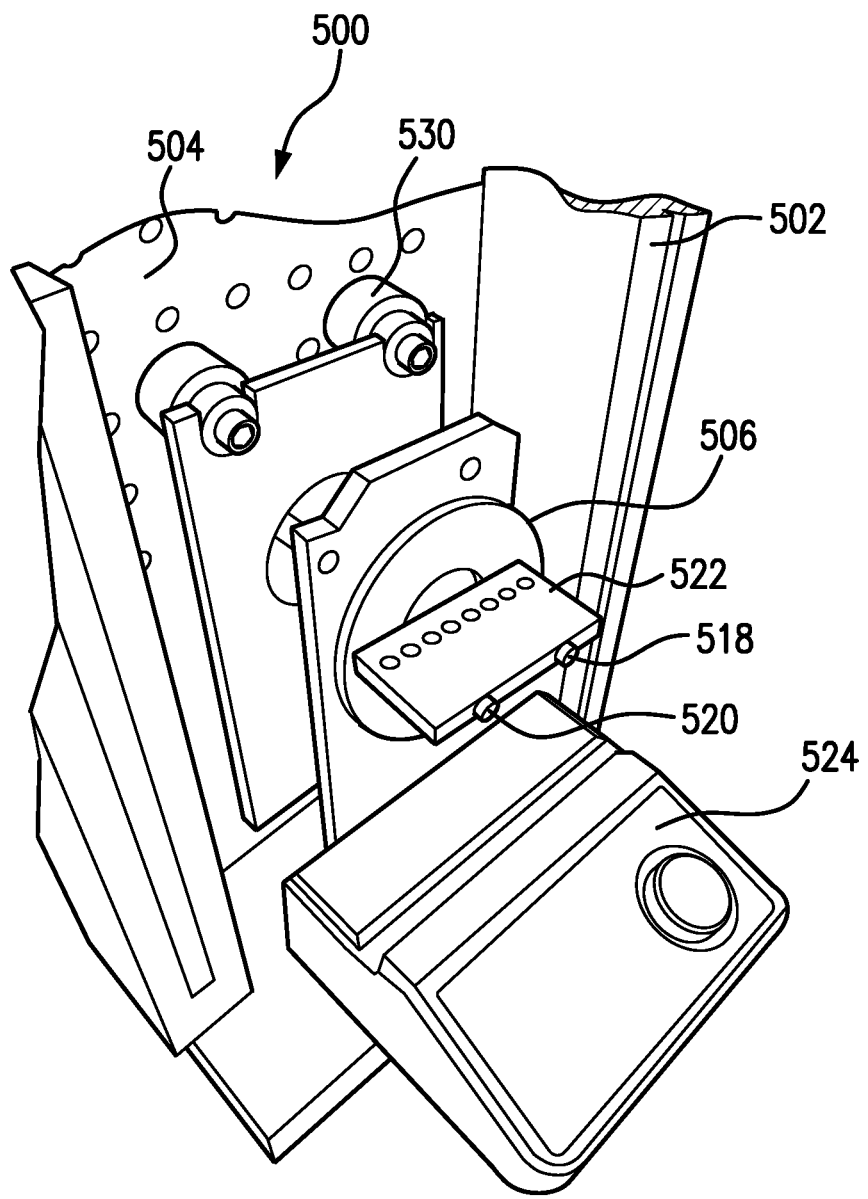
FIG. 5 is a left, top, perspective view of a system in accordance with the present invention, for translating one or more chambers, for example, a multiwell plate, along a circular cycle path on a vertical plane of movement and shows a control unit for controlling a drive motor that effects rotation of a central circular disk and thus the speed of cycling.

FIG. 5 is a left, top, perspective view of a system in accordance with the present invention, for translating one or more chambers, for example, a multiwell plate, along a circular cycle path on a vertical plane of movement, and shows a control unit for controlling a drive motor that effects rotation of a central circular disk and thus the speed of cycling. An exemplary system implementing the features shown in FIG. 4 is demonstrated by system 500 shown in FIG. 5. System 500 comprises a frame 502, a vertical mounting board 504, a rotatable circular disc 506, and threaded mounting pins 518 and 520 that extend through a multiwell plate 522 that is secured to mounting pins 518 and 520 with nuts. A variable speed motor and drive train is configured to rotate circular disc 506 about a central axis of rotation and the speed of the variable speed motor is controlled by a control unit 524. Multiwell plate 522 is secured to circular disc 506 in an off-centered swiveling arrangement as described above in connection with FIG. 4.

While the cycle path provided by the systems shown in FIGS. 4 and 5 are circular cycle paths, it is to be understood that through the use of slots, slides, mounting the circular rotating discs on yet other rotating discs, or the like features, cycle paths of other shapes and more complex patterns can be achieved.

The present invention includes the following numbered aspects, embodiments, and features, in any order and/or in any combination:

1. A method of producing an aqueous fluid-in-oil emulsion, the method comprising the steps of
    introducing an aqueous fluid and a continuous phase fluid that is immiscible with the aqueous fluid, into a chamber, wherein the density of the continuous phase fluid is greater than the density of the aqueous fluid, and
    translating the chamber along a cycle path for a plurality of cycles, the cycle path comprising at least a path portion disposed on a plane of movement, the plane of movement being angled with respect to a horizontal plane, wherein the translating comprises maintain the chamber in a fixed orientation with respect to the horizontal plane throughout the entire cycle path.

2. The method of any preceding or following embodiment/feature/aspect, wherein the chamber has a central axis and the fixed orientation comprises the central axis being perpendicular to the horizontal plane.

3. The method of any preceding or following embodiment/feature/aspect, wherein the cycle path is a two-dimensional path entirely on the plane of movement and the translating comprises moving the chamber in both Y axis directions and X axis directions on the plane of movement.

4. The method of any preceding or following embodiment/feature/aspect, wherein the cycle path is a three-dimensional path and the translating comprises moving the chamber in both Y axis directions and X axis directions on the plane of movement and moving the chamber in Z axis directions toward and away from the plane of movement.

5. The method of any preceding or following embodiment/feature/aspect, wherein the translating comprises moving the chamber in Z axis directions, toward, away from, and through the plane of movement.

6. The method of any preceding or following embodiment/feature/aspect, wherein the translating comprises oscillating the chamber along a first path defined by the formula $A \sin(\omega_1 \cdot t)$, where A is the amplitude of the oscillation, $\omega_1$ is $2\pi$ over the frequency of oscillation, and t is time, to form an emulsion.

7. The method of any preceding or following embodiment/feature/aspect, further comprising translating the chamber in a direction perpendicular to the first path along a second path defined by $B \sin(\omega_2 \cdot t + \varphi)$, where B is the amplitude of the translation in a direction perpendicular to A, $\omega_2$ is $2\pi$ over the frequency of oscillation, t is time, and $\varphi$ is phase.

8. The method of any preceding or following embodiment/feature/aspect, wherein the chamber remains substantially vertical throughout the oscillating step.

9. The method of any preceding or following embodiment/feature/aspect, wherein ω2 equals ω1.

10. The method of any preceding or following embodiment/feature/aspect, wherein the oscillation of the chamber occurs substantially along a vertical axis as defined by normal to a horizontal surface.

11. The method of any preceding or following embodiment/feature/aspect, wherein the cycle path is not perpendicular to the horizontal plane.

12. The method of any preceding or following embodiment/feature/aspect, wherein the cycle path is neither perpendicular nor parallel to the horizontal plane.

13. The method of any preceding or following embodiment/feature/aspect, wherein the plane of movement of the cycle path is tilted at least 30 degrees relative to the horizontal plane.

14. The method of any preceding or following embodiment/feature/aspect, wherein the plane of movement of the cycle path is tilted at least 45 degrees relative to the horizontal plane.

15. The method of any preceding or following embodiment/feature/aspect, wherein the plane of movement of the cycle path is tilted at least 60 degrees relative to the horizontal plane.

16. The method of any preceding or following embodiment/feature/aspect, wherein the chamber comprises a plurality of chambers, the introducing comprises introducing the aqueous fluid and the continuous phase fluid into the plurality chambers, and translating all of the plurality of chambers along the cycle path.

17. The method of any preceding or following embodiment/feature/aspect, wherein the chamber comprises a plurality of chambers, the introducing comprises introducing the aqueous fluid into at least one of the chambers and introducing a different aqueous fluid into at least a different one of the chambers.

18. The method of any preceding or following embodiment/feature/aspect, further comprising introducing the continuous phase fluid into the plurality of chambers, and translating all of the plurality of chambers along the cycle path.

19. The method of any preceding or following embodiment/feature/aspect, wherein the plurality of chambers comprises wells in a microtitre plate.

20. The method of any preceding or following embodiment/feature/aspect, wherein the plurality of chambers comprises separate containers that are independent of one another.

21. The method of any preceding or following embodiment/feature/aspect, wherein the chamber comprises a plurality of chambers and each chamber of the plurality of chambers has a volume of less than 1 milliliter.

22. The method of any preceding or following embodiment/feature/aspect, wherein each chamber of the plurality of chambers has a volume of less than 100 microliters.

23. The method of any preceding or following embodiment/feature/aspect, wherein the translating comprises moving the chamber along the cycle path at a speed of at least 500 cycles per minute.

24. The method of any preceding or following embodiment/feature/aspect, wherein the translating comprises moving the chamber along the cycle path at a speed of at least 1000 cycles per minute.

25. The method of any preceding or following embodiment/feature/aspect, wherein the translating comprises moving the chamber along the cycle path at a speed of at least 5000 cycles per minute.

26. The method of any preceding or following embodiment/feature/aspect, wherein the cycle path comprises a circular path.

27. The method of any preceding or following embodiment/feature/aspect, wherein the ratio of the volume of aqueous fluid to the volume of continuous phase fluid in the chamber is from 5:1 to 1:20.

28. The method of any preceding or following embodiment/feature/aspect, wherein the ratio of the volume of aqueous fluid to the volume of continuous phase fluid in the chamber is from 5:1 to 1:20.

29. The method of any preceding or following embodiment/feature/aspect, wherein the translating is carried out for at least one 10 seconds.

30. The method of any preceding or following embodiment/feature/aspect, wherein the translating is carried out for at least 3 minutes.

31. The method of any preceding or following embodiment/feature/aspect, wherein the aqueous fluid contains a DNA polymerase.

32. The method of any preceding or following embodiment/feature/aspect, wherein the aqueous fluid further comprises at least one pair of amplification primers.

33. The method of any preceding or following embodiment/feature/aspect, wherein φ does not equal 0.

34. The method of any preceding or following embodiment/feature/aspect, wherein φ is in the range of from greater than 0 to less than or equal to 90 degrees.

35. A system for producing an aqueous fluid-in-oil emulsion, the system comprising:
a mounting frame;
a drive train including a drive motor mounted on the mounting frame; and
a chamber platform connected to the drive train, wherein the drive train is configured to move the chamber platform along a cycle path that includes a vertical component, and the chamber platform is connected to the drive train through a swiveling connection such that the chamber platform maintains predetermined orientation with respect to a horizontal surface throughout movement along the entire cycle path.

36. The system of any preceding or following embodiment/feature/aspect, wherein the cycle path is a circular cycle path along a plane of movement that is perpendicular to a horizontal surface.

37. The system of any preceding or following embodiment/feature/aspect, wherein the drive motor comprises a variable speed drive motor.

38. The system of any preceding or following embodiment/feature/aspect, further comprising a multiwell plate secured to the chamber platform.

39. The system of any preceding or following embodiment/feature/aspect, wherein the multiwell plate comprises a plurality of wells, at least one well of the wells of the plurality contains an aqueous fluid and an oil, the aqueous fluid has a density, the oil has a density that is greater than the density of the aqueous fluid, and the at least one well is sealed.

40. The system of any preceding or following embodiment/feature/aspect, further comprising a vial secured to the chamber platform.

41. The system of any preceding or following embodiment/feature/aspect, wherein the vial contains an aqueous fluid and an oil, the aqueous fluid has a density, the oil has a density that is greater than the density of the aqueous fluid, and the vial is sealed.

42. The system of any preceding or following embodiment/feature/aspect, further comprising a chamber secured to the chamber platform, wherein the chamber contains an aqueous fluid and an oil, the aqueous fluid has a density, the oil has a density that is greater than the density of the aqueous fluid, the chamber is sealed, and the aqueous fluid contains a DNA polymerase and at least one pair of amplification primers.

43. The system of any preceding or following embodiment/feature/aspect, wherein the drive train comprises a rotatable circular disk and an off-centered swivel mount mounted to the rotatable circular disk for swiveling motion, and the chamber platform comprises at least two mounting pins secured to the off-centered swivel mount.

44. The system of any preceding or following embodiment/feature/aspect, wherein the cycle path is on a plane of movement that is tilted with respect to a horizontal surface.

45. The system of any preceding or following embodiment/feature/aspect, wherein the plane of movement is tilted at an angle of from about 15 degrees to about 75 degrees with respect to the horizontal surface.

46. The system of any preceding or following embodiment/feature/aspect, wherein the plane of movement is tilted at an angle of from about 30 degrees to about 60 degrees with respect to the horizontal surface.

The present invention can include any combination of these various features or embodiments above and/or below as set forth in sentences and/or paragraphs. Any combination of disclosed features herein is considered part of the present invention and no limitation is intended with respect to combinable features.

OTHER EMBODIMENTS

The foregoing has been a description of certain non-limiting embodiments of the invention. Those of ordinary skill in the art will appreciate that various changes and modifications to this description may be made without departing from the spirit and scope of the present invention, as defined in the following claims.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members, are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permit the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

All publications, including, but not limited to, journal articles, books, patents, and patent applications, cited in this specification, are herein incorporated by reference in their entireties as if each individual publication were specifically and individually indicated to be incorporated by reference herein. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain, using no more than routine experimentation, many equivalents to the specific embodiments described herein. The scope of the present embodiments described herein is not intended to be limited to the above description, but rather is as set forth in the appended claims. Those of ordinary skill in the art will appreciate that various changes and modifications to this description may be made without departing from the spirit and scope of the present invention, as defined in the following claims.

What is claimed is:

1. A system for producing an aqueous fluid-in-oil emulsion, the system comprising:
    a mounting frame;
    a drive train including a drive motor mounted on the mounting frame and a rotatable disk mounted on the mounting frame for rotation about a fixed horizontal axis of rotation; and
    a chamber platform connected to the rotatable disk, wherein
    the drive train is configured to rotate the rotatable disk about the fixed horizontal axis of rotation and move the chamber platform along a cycle path on a vertical plane of movement, and
    the chamber platform is connected to the rotatable disk through a swiveling connection such that the chamber platform maintains a predetermined orientation with respect to a horizontal surface throughout movement along the entire cycle path.

2. The system of claim 1, wherein the drive motor comprises a variable speed drive motor.

3. The system of claim 1, further comprising a multiwell plate secured to the chamber platform.

4. The system of claim 3, wherein the multiwell plate comprises wells in the form of vials and each of the vials is sealed by a cap.

5. The system of claim 3, wherein the multiwell plate comprises eight wells, each in the form of a vial sealed by a cap.

6. The system of claim 3, wherein the multiwell plate comprises a plurality of wells, at least one of the wells contains an aqueous fluid and an oil, the aqueous fluid has a density, the oil has a density that is greater than the density of the aqueous fluid, and the at least one well is sealed.

7. The system of claim 1, further comprising a vial secured to the chamber platform.

8. The system of claim 7, wherein the vial has a top and the system further comprises a cap sealing the vial at the top.

9. The system of claim 7, wherein the vial contains an aqueous fluid and an oil, the aqueous fluid has a density, the oil has a density that is greater than the density of the aqueous fluid, and the vial is sealed.

10. A system for producing an aqueous fluid-in-oil emulsion, the system comprising:
- a mounting frame;
- a drive train including a drive motor mounted on the mounting frame; and
- a chamber platform connected to the drive train, wherein the drive train is configured to move the chamber platform along a cycle path that includes a vertical component, and the chamber platform is connected to the drive train through a swiveling connection such that the chamber platform maintains a predetermined orientation with respect to a horizontal surface throughout movement along the entire cycle path,
the system further comprising a chamber secured to the chamber platform, wherein the chamber contains an aqueous fluid and an oil, the aqueous fluid has a density, the oil has a density that is greater than the density of the aqueous fluid, the chamber is sealed, and the aqueous fluid contains a DNA polymerase.

11. The system of claim 1, wherein the rotatable disk is a rotatable circular disk and the swiveling connection comprises an off-centered swivel mount mounted to the rotatable circular disk for swiveling motion, and the chamber platform comprises at least two mounting pins secured to the off-centered swivel mount.

12. The system of claim 1, wherein the cycle path is on a vertical plane of movement that is tilted with respect to a horizontal surface.

13. The system of claim 12, wherein the vertical plane of movement is tilted at an angle of from about 15 degrees to about 75 degrees with respect to the horizontal surface.

14. The system of claim 12, wherein the vertical plane of movement is tilted at an angle of from about 30 degrees to about 60 degrees with respect to the horizontal surface.

15. The system of claim 1, further comprising a chamber secured to the chamber platform, wherein the chamber contains an aqueous fluid and an oil, the aqueous fluid has a density, and the oil has a density that is greater than the density of the aqueous fluid.

16. The system of claim 15, wherein the aqueous fluid further contains at least one pair of amplification primers.

17. The system of claim 15, wherein the aqueous fluid contains a target DNA for amplification.

18. The system of claim 17, wherein the aqueous fluid and the oil are in the form of an emulsion comprising droplets, and the target DNA for amplification is present at a concentration such that only one target is available for amplification in one of the droplets.

19. The system of claim 10, wherein the aqueous fluid further contains at least one pair of amplification primers.

* * * * *